United States Patent [19]

Inamoto et al.

[11] 4,104,305

[45] Aug. 1, 1978

[54] 1-AMINOTRICYCLO (4.3.1.1$^{2,5}$) UNDECANE AND SALTS THEREOF

[75] Inventors: Yoshiaki Inamoto; Koji Aigami; Motoyoshi Ohsugi; Yoshiaki Fujikura; Hiroshi Ikeda, all of Wakayama, Japan

[73] Assignee: Kao Soap Co., Ltd., Tokyo, Japan

[21] Appl. No.: 839,977

[22] Filed: Oct. 6, 1977

[30] Foreign Application Priority Data

Oct. 13, 1976 [JP] Japan .................. 51-123360

[51] Int. Cl.$^2$ ............................................. C07C 87/40
[52] U.S. Cl. ............................ 260/563 P; 260/501.1; 260/501.21; 260/561 R; 424/316; 424/330
[58] Field of Search ............ 260/563 P, 501.1, 501.21

[56] References Cited

U.S. PATENT DOCUMENTS

| 3,496,228 | 2/1970 | Hoover | 260/563 |
|---|---|---|---|
| 3,579,567 | 5/1971 | Deslongchamps | 260/563 X |
| 3,845,124 | 10/1974 | Deslongchamps | 260/563 |

*Primary Examiner*—Robert V. Hines
*Attorney, Agent, or Firm*—Blanchard, Flynn, Thiel, Boutell & Tanis

[57] ABSTRACT

1-Amino-tricyclo [4.3.1.1$^{2,5}$] undecane is prepared by alkaline hydrolysis of 1-acetylamino-tricyclo [4.3.1.1$^{2,5}$] undecane, and its acid addition salts are prepared by neutralizing it with an acid. The compounds possess antiviral activity.

2 Claims, No Drawings

1-AMINOTRICYCLO (4.3.1.1$^{2,5}$) UNDECANE AND SALTS THEREOF

BACKGROUND OF THE INVENTION

Field of the Invention

The present invention relates to a tricycloundecylamine and acid addition salts thereof. More particularly, the present invention relates to 1-amino-tricyclo[4.3.1.1$^{2,5}$] undecane of the formula (I) and acid addition salts thereof:

(I)

The new compounds of the present invention, i.e. 1-aminotricyclo [4.3.1.1$^{2,5}$] undecane and acid addition salts thereof have an excellent effect of inhibiting propagation of Newcastle disease virus of Paramyxo viruses belonging to the group of RNS viruses, in embryonic cells of chickens and the toxicity thereof to the cells is relatively low. Namely, the compounds of the invention inhibit the propagation of the virus even if they are used in a low concentration of about one-third the concentration of adamantylamine hydrochloride which is effective for the same purpose. Adamantylamine hydrochloride is a well-known antiviral substance against influenza. The compounds of the invention are thus useful substances as active ingredients of medicines for human beings and animals.

Elementary analysis and mass spectrum analysis of the new compound of the present invention, i.e. 1-aminotricyclo [4.3.1.1$^{2,5}$] undecane (I), and acid addition salts thereof indicate that they are compounds containing only one nitrogen atom. Further, the structures of these compounds have been confirmed from the facts that absorptions peculiar to the amine group (3325, 3250 cm$^{-1}$) are shown in the infrared absorption spectrum and the substitution position of the starting material used for the synthesis of (I), i.e. 1-acetylaminotricyclo [4.3.1.1$^{2,5}$] undecane, is the 1-position.

The compound of formula (I) of the present invention can be synthesized by hydrolysis of the corresponding N-acetylated compound, i.e. 1-acetylaminotricyclo [4.3.1.1$^{2,5}$] undecane of formula (II):

(II)

The hydrolysis can be carried out under any reaction conditions effective for general alkaline hydrolysis of amides. In other words, the desired 1-aminotricyclo [4.3.1.1$^{2,5}$] undecane of formula (I) can be obtained by hydrolyzing 1-acetylaminotricyclo [4.3.1.1$^{2,5}$] undecane of formula (II) in an aqueous solution of an alkali or in the presence of an alkali in an alcohol or a mixture of water and an alcohol as solvent. As the alkali used for the hydrolysis, there can be mentioned alkali metal hydroxides such as sodium hydroxide and potassium hydroxide and alkali metal carbonates such as sodium carbonate and potassium carbonate. The alcohols include lower alcohols such as methanol, ethanol and propanol and glycols such as ethylene glycol, propylene glycol and diethylene glycol. The reaction temperature is in the range of 10° to 350° C, preferably 60° to 300° C, more preferably 170° to 245° C.

The acid addition salts of the formula (I) compound are obtained easily by neutralization of the thus-obtained compound of formula (I). The acids used include mineral acids such as hydrochloric acid, hydrobromic acid, hydroiodic acid, sulfuric acid, thiosulfuric acid and phosphoric acid and organic acids such as p-toluenesulfonic acid, formic acid, acetic acid, propionic acid, oxalic acid and citric acid. Among those acids, hydrohalogenic acids such as hydrochloric acid, hydrobromic acid and hydroiodic acid are convenient and preferred.

1-Acetylaminotricyclo [4.3.1.1$^{2,5}$] undecane of formula (II) used as the starting material in the present invention can be obtained easily by, for example, reacting a 2-halogenotricyclo [4.3.1.1$^{2,5}$] undecane, 1-hydroxytricyclo [4.3.1.1$^{2,5}$] undecane or endo-1-hydroxymethyl-exo-2,3-trimethylenenorbornane with acetonitrile in the presence of sulfuric acid.

The following examples further illustrate the present invention. Processes for the synthesis of the starting material are also shown in the Preparations.

EXAMPLE 1

A solution comprising a mixture of 13.0 g (63 millimoles) of 1-acetylaminotricyclo [4.3.1.1$^{2,5}$] undecane of formula (II), 8.4 g (210 millimoles) of sodium hydroxide and 160 ml of diethylene glycol is refluxed under stirring for 15.5 hours. After allowing the solution to cool, the reaction solution is poured into water and is extracted with 200 ml of diethyl ether. The ether solution is washed with water and dried with anhydrous sodium sulfate. The ether is distilled out and the resulting residue is subjected to fractional distillation under reduced pressure to collect a fraction having a boiling point of 65°–66° C/1.0 mmHg. Thus 9.40 g (yield: 90.4%) of 1-aminotricyclo [4.3.1.1$^{2,5}$] undecane are obtained. After allowing the product to cool, white crystals of a melting point of 111°–113° C are obtained.

Elementary analysis:
  Found: C, 79.75: H, 11.57: N, 8.68%
  Calculated as C$_{11}$H$_{19}$N: C, 80.00: H, 11.52: N, 8.48%
IR (KBr, cm$^{-1}$):
  3325, 3250, 3015, 1590, 1460, 1120, 820
Mass spectrum m/e (relative intensity):
  165 (0.3, M$^+$), 122 (19), 97 (8), 96 (100), 79 (5), 67 (6)

EXAMPLE 2

Dry hydrogen chloride gas is introduced in a solution of 1.0 g (6 millimoles) of 1-aminotricyclo [4.3.1.1$^{2,5}$] undecane of formula (I) in 15 ml of anhydrous diethyl ether to form a white precipitate. The precipitate is filtered off, dried and recrystallized from acetone-methanol to obtain 1.1 g (yield: 91%) of 1-aminotricyclo [4.3.1.1$^{2,5}$] undecane hydrochloride.

Elementary analysis:
  Found: C, 65.1; H, 9.7; N, 6.9; Cl, 17.9
  Calculated as C$_{11}$H$_{20}$NCl: C, 65.4; H, 10.0; N, 6.9; Cl, 17.6
IR (KBr, cm$^{-1}$):
  3050, 2900, 2870, 1620, 1605, 1595, 1505, 1470, 1375

EXAMPLE 3

Embryonic cells of chickens were subjected to single-layer culture in a test tube for 2-3 days and then inoculated with about 128 HAU (hemagglutination units) of Newcastle disease virus. To the upper layer thereof there was added a medium containing the following compounds of various concentrations stepwise as shown below. After culturing at 37° C for 48 hours, the effect was determined according to the coagulation reaction of erythrocytes. The results are shown in the following table:

| Compound | Conc. (μg/ml) | % HAU* | CT** |
| --- | --- | --- | --- |
| 1-Aminotricyclo- | 347 | 1.0 | + |
| [4.3.1.1$^{2,5}$]- | 174 | 1.0 | + |
| undecane | 87 | 2 | + |
| hydrochloride | 44 | 25 | − |
| (present invention) | 22 | 42 | − |
| Adamantylamine | 500 | 1.0 | + |
| hydrochloride | 250 | 9 | + |
| (control) | 125 | 100 | − |
|  | 62 | 100 | − |

*%HAU = $\dfrac{\text{HAU (Dilution multiple controlling coagulation of erythrocytes) of the sample containing the compound}}{\text{HAU of the blank sample}} \times 100$

**CT: Degrees of damage of the embryonic cells of chicken caused by the compound:
(−) No damage
(±) The cell surface had slight rashes
(+) Monolayer cells were parted from the wall of the test tube.

Preparation 1

1.0 Gram (4.8 millimoles) of tricyclo [4.3.1.1$^{2,5}$] undecane is added to 2 ml (38.7 millimiles) of liquid bromine and the mixture is stirred at room temperature for 17 hours. The reaction mixture is added slowly to a cooled saturated solution of sodium hydrogensulfite under stirring to remove excess bromine. The aqueous solution is extracted twice, each time with 20 ml of carbon tetrachloride and the extract is dried with magnesium sulfate. Carbon tetrachloride is distilled off and the residue (1.9 g) is distilled under reduced pressure to collect a fraction boiling at 96°-8° C/2mmHg . 1.0 Gram (yield: 65.5%) of 1-bromotricyclo [4.3.1.1$^{2,5}$] undecane is thus obtained. Upon cooling, white crystals having a melting point of 57.5°-58.5° C are obtained.

Elementary analysis:
 Found: C, 57.2; H, 7.4; Br, 34.2%
 Calculated as $C_{11}H_{17}Br$: C, 57.7; H, 7.5; Br, 34.9%
IR (Nujol, cm$^{-1}$):
 3030, 1295, 1240, 1155, 1060, 1000, 995, 960, 760
$^1$HNMR (CDCl$_3$ solvent, TMS internal standard, δ)
 0.8-2.8 (multiplet)
$^{13}$CNMR (CDCl$_3$ solvent, TMS internal standard, δ c):
 22.46(t), 26.52(t), 27.98(t and t), 34.27(t), 37.77(d), 39.35(t), 39.80(d), 41.18(t), 51.41(d), 75.08(s)

Mass spectrum m/e (relative intensity):
 230(0.1, M$^+$), 229(0.2, M$^+$), 150(13), 149(100), 107(15),
 91(15), 83(18), 81(44), 79(23), 67(8)

Preparation 2

1.18 Gram (5.1 millimoles) of 1-bromotricyclo [4.3.1.1$^{2,5}$] undecane are dissolved in 10 ml of acetonitrile. The solution is cooled and kept at 0° C, and then 2.5 ml of concentrated sulfuric acid are added dropwise under cooling over 30 minutes. The stirring is continued further at room temperature for 20 hours.

The reaction mixture is placed on 200 g of ice and extracted twice, each time with 100 ml of diethyl ether. The extract is washed with saturated aqueous solution of sodium hydrogen carbonate and then with water and thereafter dried with anhydrous sodium sulfate. The solvent is distilled off and the residue is recrystallized from acetone-n-hexane to give 0.98 g (yield: 92%) of 1-acetylaminotricyclo [4.3.1.1$^{2,5}$] undecane (II) as white crystals (m.p. 138°-139° C).

Elementary analysis:
 Found: C, 75.21; H, 10.20; N, 6.34%
 Calculated as $C_{13}H_{21}NO$: C, 75.36; H, 10.14; N, 6.76%
IR (KBr, cm$^{-1}$):
 3325, 3070, 1680, 1650, 1550, 1470, 1370, 1310, 1280, 1125

Mass spectrum m/e (relative intensity)
 207(14, M$^+$), 164(45), 138(100), 96(8), 87(12)

Additional details of the preparation of the formula (II) compound are disclosed in Japanese Ser. No. 122440/76, filed Oct. 12, 1976, corresponding to U.S. Ser. No. 839,976, filed Oct. 6, 1977, the entire contents of which are incorporated herein by reference.

The embodiments of the invention in which an exclusive property or privilege is claimed are defined as follows:

1. 1-Aminotricyclo [4.3.1.1$^{2,5}$] undecane having the formula (I):

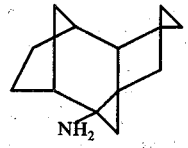

and acid addition salts thereof.

2. The hydrochloric acid, hydrobromic acid or hydroiodic acid addition salt of 1-aminotricyclo [4.3.1.1$^{2,5}$] undecane of formula (I) according to claim 1.